United States Patent
Siccardi et al.

(10) Patent No.: US 10,939,924 B2
(45) Date of Patent: Mar. 9, 2021

(54) INSTRUMENT FOR BONE RESECTION (71) Applicant: MEDACTA INTERNATIONAL SA, Castel San Pietro (CH)

(72) Inventors: Francesco Siccardi, Castel San Pietro (CH); Massimiliano Bernardoni, Castel San Pietro (CH); Anna Sassi, Castel San Pietro (CH); Fabio Burgassi, Castel San Pietro (CH); Alessio Beccari, Castel San Pietro (CH)

(73) Assignee: MEDACTA INTERNATIONAL SA, Castel San Pietro (CH)

( * ) Notice: Subject to any disclaimer, the term of this patent is extended or adjusted under 35 U.S.C. 154(b) by 152 days.

(21) Appl. No.: 16/085,451

(22) PCT Filed: Mar. 1, 2017

(86) PCT No.: PCT/IB2017/051191
§ 371 (c)(1),
(2) Date: Sep. 14, 2018

(87) PCT Pub. No.: WO2017/158459
PCT Pub. Date: Sep. 21, 2017

(65) Prior Publication Data
US 2019/0076155 A1 Mar. 14, 2019

(30) Foreign Application Priority Data
Mar. 16, 2016 (IT) .................. 102016000027433

(51) Int. Cl.
*A61B 17/15* (2006.01)
*A61B 90/00* (2016.01)
(Continued)

(52) U.S. Cl.
CPC ........ *A61B 17/157* (2013.01); *A61B 17/1675* (2013.01); *A61B 17/1764* (2013.01);
(Continued)

(58) Field of Classification Search
CPC ..... A61B 17/15; A61B 17/154; A61B 17/157; A61B 17/1675
See application file for complete search history.

(56) References Cited

U.S. PATENT DOCUMENTS

| 7,641,661 B2* | 1/2010 | Steffensmeier | A61B 17/157 606/88 |
| 2013/0116698 A1* | 5/2013 | Wilkinson | A61B 17/157 606/88 |

(Continued)

FOREIGN PATENT DOCUMENTS

| GB | 2447702 A | 9/2008 |
| JP | 2010125202 A | 6/2010 |

(Continued)

OTHER PUBLICATIONS

International Search Report and Written Opinion for PCT Application No. PCT/IB2017/051191, dated May 29, 2017, 10 pages.

(Continued)

*Primary Examiner* — Larry E Waggle, Jr.
(74) *Attorney, Agent, or Firm* — Meunier Carlin & Curfman LLC (57) ABSTRACT

A bone resection instrument, comprising means of support and positioning (2) for the correct alignment of the tool (1) with respect to the bone to be cut, a cutting guide (7), connected to the means of support and positioning (2), comprising a support (8) attachable to a bone to be cut. The cutting guide (7) comprises a gauge block (9) having a cutting surface (90) and removably connected to said support (8). The instrument (1) is part of a bone resection kit comprising a plurality of gauge blocks (9), each differing in height (h) from one another.

9 Claims, 12 Drawing Sheets

(51) Int. Cl.
*A61B 17/16* (2006.01)
*A61B 17/17* (2006.01)
*A61B 17/56* (2006.01)

(52) U.S. Cl.
CPC .............. *A61B 90/06* (2016.02); *A61B 17/15* (2013.01); *A61B 2017/568* (2013.01); *A61B 2090/061* (2016.02)

(56) References Cited

U.S. PATENT DOCUMENTS

| | | | |
|---|---|---|---|
| 2013/0144296 A1* | 6/2013 | Yoko | A61B 17/1604 606/84 |
| 2013/0184713 A1* | 7/2013 | Bojarski | A61B 17/1764 606/88 |
| 2013/0296874 A1 | 11/2013 | Chao | |

FOREIGN PATENT DOCUMENTS

| | | | | |
|---|---|---|---|---|
| JP | 2013248399 A | 12/2013 | | |
| JP | 2014176669 A | 9/2014 | | |
| WO | 00/071035 A1 | 11/2000 | | |
| WO | WO-0071035 A1 * | 11/2000 | ........... | A61B 17/157 |
| WO | 2012/158604 A1 | 11/2012 | | |

OTHER PUBLICATIONS

English Translation of Notice of Reasons for Refusal issued in JP Application No. 2018-548823, dated Sep. 11, 2019.

* cited by examiner

INSTRUMENT FOR BONE RESECTION

The present invention relates to a instrument for bone resection, a bone resection kit and a method for assembling such an instrument.

In arthroplasty of the knee and in particular in unicompartmental arthroplasty, there is evidence of the need for users to carry out more conservative bone resections, allowing them to make the smallest possible cut compatible with the thickness of the prosthesis while preserving the greatest possible extent of non-pathological subchondral bone.

This makes it possible to position the implant at a level such that the quality of the bone is optimal for supporting the joint load, reducing the risk of the prosthesis sinking when subjected to physiological loads.

This result can be obtained through a surgical technique and instrumentation which together make it possible to progressively correct the cut with small height changes, starting from a minimum cut height defined in the operative or pre-operative phase.

In other words, a first cut is made in a more proximal position, gradually shifting the cut line progressively lower until reaching the desired position. With the instruments currently commercially available, the positioning of the cutting guide, suitable to ensure desired parameters such as slope angle, varus/valgus and cut height, can be defined in the operating room with intramedullary or extramedullary reference systems from anatomical reference points. In particular, the cut height can be defined with a probe with respect to the anatomical reference points (for example, a more distal point from the pathological glenoid) or using an "eyeballing" technique, i.e. via a visual identification by the surgeon of the level of resection to be performed.

Alternatively, the positioning of the cutting guide can also be defined pre-operatively, with planning based on an analysis of the status of the bone by CT or MRI. Such planning does not usually make it possible to perform an assessment of the condition of the ligaments and soft tissues. The positioning of the cutting guide is carried out with a patient-specific positioner that makes it possible to achieve the parameters determined in the pre-operative phase.

The patient-specific positioner is understood as an instrument, or part of an instrument, presenting the anatomical reference points of the surgical patient. This instrument is manufactured ad hoc based on the anatomy of the part being operated on, taking as reference points anatomical details (for example, osteophytes) against which the matching points of the instrument check, thus making possible the unique and stable positioning of the instrument.

Using one of the techniques described above, the position of the cutting block is defined, the cutting block being attached to the bone by means of two or more pegs or pins.

If the first resection or the first positioning of the cutting block is not satisfactory in terms of cut height (for example because the knee is too tight or the quality of the bone at the level of the cutting plane is not good enough to allow a stable implant of the prosthesis), it can be corrected by removing additional bone thickness.

With the instruments currently commercially available, the correction of the cut height can be carried out by repositioning the cutting block on its pins using the more proximal holes (if the cutting block is provided with a plurality of holes pre-aligned at several levels), or by removing the pins and moving the guide distally using a micrometric adjustment system (if provided) or again via an "eyeballing" technique, i.e. via a visual identification, subsequently securing the guide with two or more pegs.

The Applicant has noted drawbacks in all the abovementioned cases and seeks to overcome them with the present invention.

In particular, the functional limitations relating to the repositioning of the cutting block on its pins using suitable more proximal holes are due to the fact that the cutting block can be moved to discrete heights, the minimum value of which is constrained by the geometric limitation of providing equally spaced rows of holes with diameters equal to those of the pins; this value is in certain cases considered excessive for a minimal and conservative correction of the cut height. This type of repositioning also entails the risk of changing the initially obtained alignment by accidentally changing the inclination of the pins previously attached to the bone (during the removal and reinsertion of the cutting block on its pins) or due to dimensional differences between the various holes and their relative positions.

The alternative of removing the pins and moving the guide distally using a micrometric adjustment system (if provided) or via an "eyeballing" technique, however involves the complete realignment of the guide with the risk of changing the previously defined cutting parameters (slope angles, varus/valgus), that need to be kept constant during the height correction. This surgical procedure thus inevitably takes a long time. This technique is also particularly invasive because pins are removed and repositioned causing a further weakening of the bone.

It is clear from the abovementioned drawbacks that there is a need to provide a bone resection instrument that can remedy these drawbacks.

A purpose of the present invention is therefore to provide a bone resection instrument which makes it possible to vary the cut height without the need to remove and replace the pins in a different location.

Another purpose of the present invention is to provide a bone resection instrument which makes it possible to vary the level of bone resection, reducing the surgical procedure and making it as minimally invasive as possible.

A further purpose of the present invention is to provide a bone resection instrument which makes it possible to keep the cutting parameters unchanged while varying the cut height.

A still further purpose of the present invention to provide a bone resection kit that is able to provide the surgeon with the abovementioned benefits.

It is also a purpose of the present invention to provide a method of assembling the bone resection instrument that makes it possible to easily and quickly assemble the bone resection instrument in the operative phase.

These and other purposes are substantially achieved by a bone resection instrument as described in one or more of the accompanying claims.

A further purpose of the present invention is to provide a method of assembling the aforementioned bone resection instrument, as proposed in one of the appended claims.

Finally, it is a further purpose of the present invention to provide a bone resection kit, as proposed in one or more of the appended claims.

Further beneficial characteristics are described in the dependent claims.

The present invention will become more apparent from the detailed description that follows, with reference to the accompanying drawings provided purely by way of example, in which:

FIG. 10 is a representation of the instrument of the present invention according to the configuration illustrated in FIG. 2 in use, in which the cutting guide is associated with a patient-specific positioner to correctly align and position the bone resection instrument to the body being operated on;

In the attached figures, the bone resection instrument according to the present invention is indicated by 1.

It comprises means for supporting and positioning 2 which are used for the correct alignment of the instrument 1 with respect to the bone to be cut, in particular for correctly positioning and associating it with the anatomical part to be operated on.

Specifically, the supporting and positioning means2 comprise an extramedullary or intramedullary positioning system.

Such supporting and positioning means2 can be adjusted in height with respect to a transverse plane, laterally with respect to the sagittal plane and in inclination (the so-called slope angle) with respect to the transverse plane, to position and align the tool with respect to the point at which the surgeon must operate.

Figure 1:
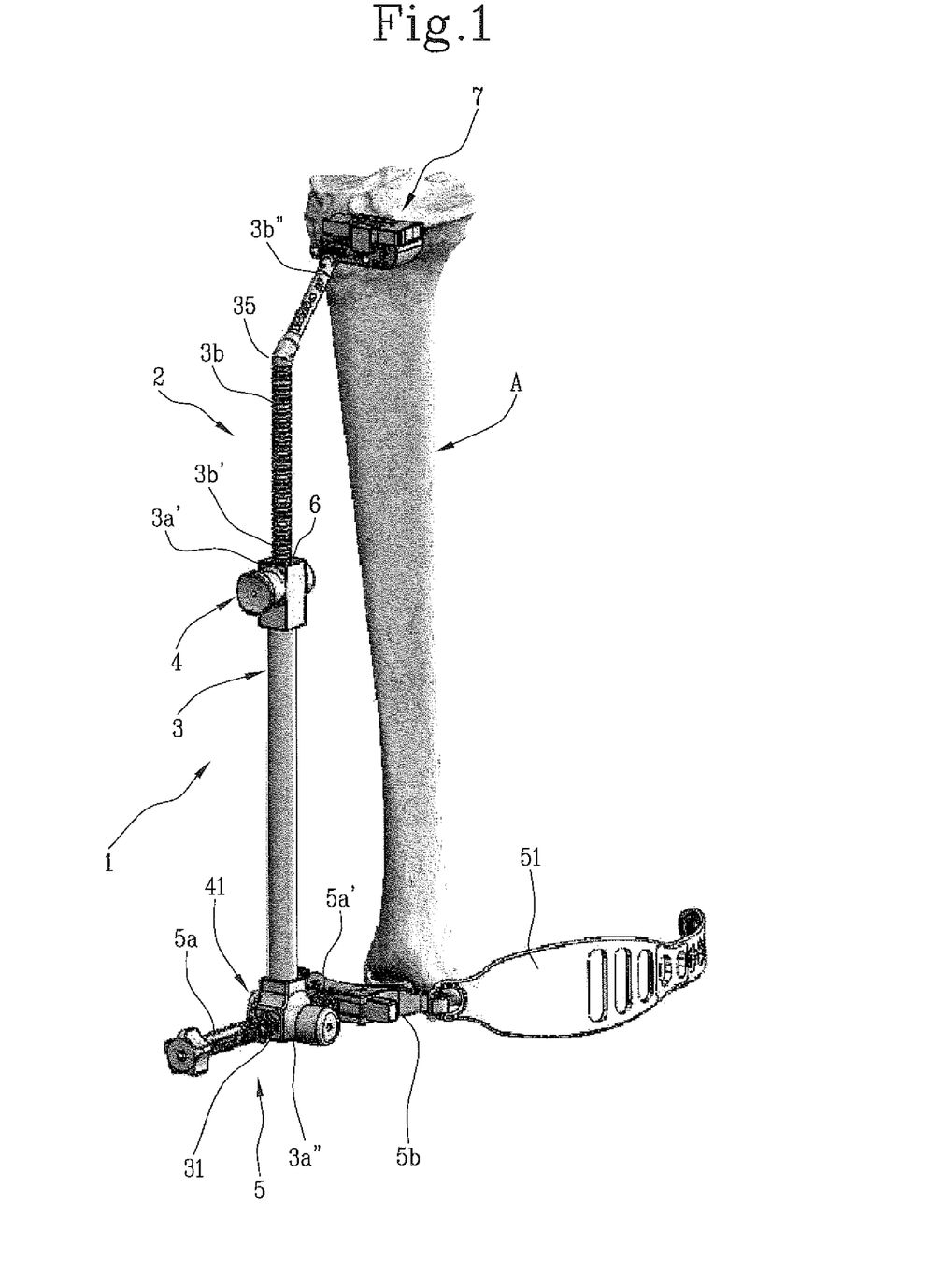
FIG. 1 is a perspective view of a bone resection instrument according to the present invention in use.

By way of example only, an extramedullary system is described below and illustrated in FIG. 1, comprising an extendable rod 3, composed of a first portion 3a and a second portion 3b insertable, by its first end 3b', into the first portion 3a. For this purpose, the first portion 3a has an axial cavity 6 which is open at a first end 3a' thereof.

A locking and unlocking mechanism 4 permits the relative movement of the two parts and the corresponding block into the desired position. Using this locking and unlocking mechanism 4, the second portion 3b is adjustable in height in a controlled manner with respect to the first portion 3a of the rod, to position the correct part of the cutting guide 7 in correspondence with a second end 3b" of the second portion 3b of the rod 3.

The extramedullary supporting and positioning means2 also comprise a base 5, which is suitable to mate with the limb A or the part of the anatomy of the patient. The base 5 may comprise an arm 5a, orthogonal to the rod 3, and a collar 5b suitable to engage with the part of the anatomy A of the patient.

The base 5 is movably attached to the rod 3.

In particular, the first portion 3a of the rod 3 has, at its second end 3a", a hole 31 in which the arm 5a is housed and can slide.

In the case of resections of tibial bones, for example, the collar 5b, having a concave profile, is associated with the ankle and is fastened to it by means of a rubber band, a strap, an ankle band or other similar devices.

The rod 3 can be moved along the arm 5a, always maintaining a perpendicular arrangement between the two components.

A locking and unlocking mechanism 41, similar to the one that allows the relative movement between the first portion 3a and the second portion 3b of the rod 3, regulates the movement between the rod 3 and the arm 5a, to move the rod 3, and thus the cutting guide 7, closer or further away from the part of the anatomy of the patient which must be operated on. By means of said locking and unlocking mechanism 41, it is also possible to adjust the inclination of the rod 3b in the sagittal plane in order to change the slope angle.

The collar 5b is positioned at one end 5a' of the arm 5a.

The means of support and positioning 2 are also adjustable with respect to a sagittal plane, through a lateral relative movement with respect to the sagittal plane between the collar 5b and the arm 5a.

The bone resection instrument 1 also comprises a cutting guide 7, suitable to guide the blade during cutting.

This guide 7, connected to said means of support and positioning 2, comprises a support 8 which can be attached to the bone to be cut and a gauge block 9 (or shim) that defines the actual cutting surface 90. The gauge block 9 is removably connected to the support 8.

The support 8 can typically be attached to the bone by means of a plurality of pins 30 (as shown in FIGS. 10-13) which can be inserted through a corresponding number of holes 10 present in the support 8.

Figures 7A, 7B, 7C, 7D, 7E:
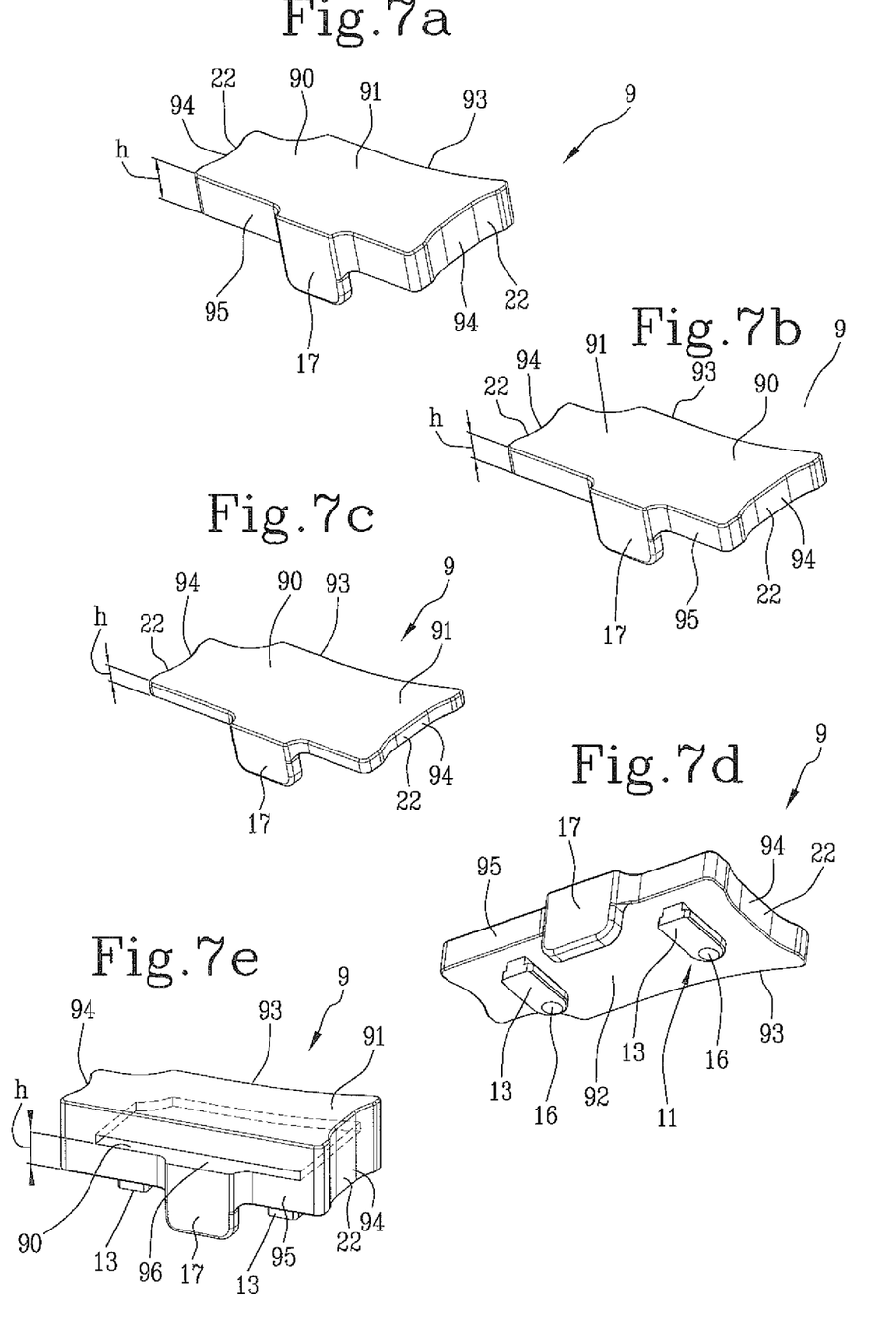
FIGS. 7a-7c are perspective views of gauge blocks having three different heights.
FIG. 7d is a perspective view from below of the gauge block of FIG. 7b.
FIG. 7e is a perspective view of an alternative configuration of the gauge block.
Figure 8:
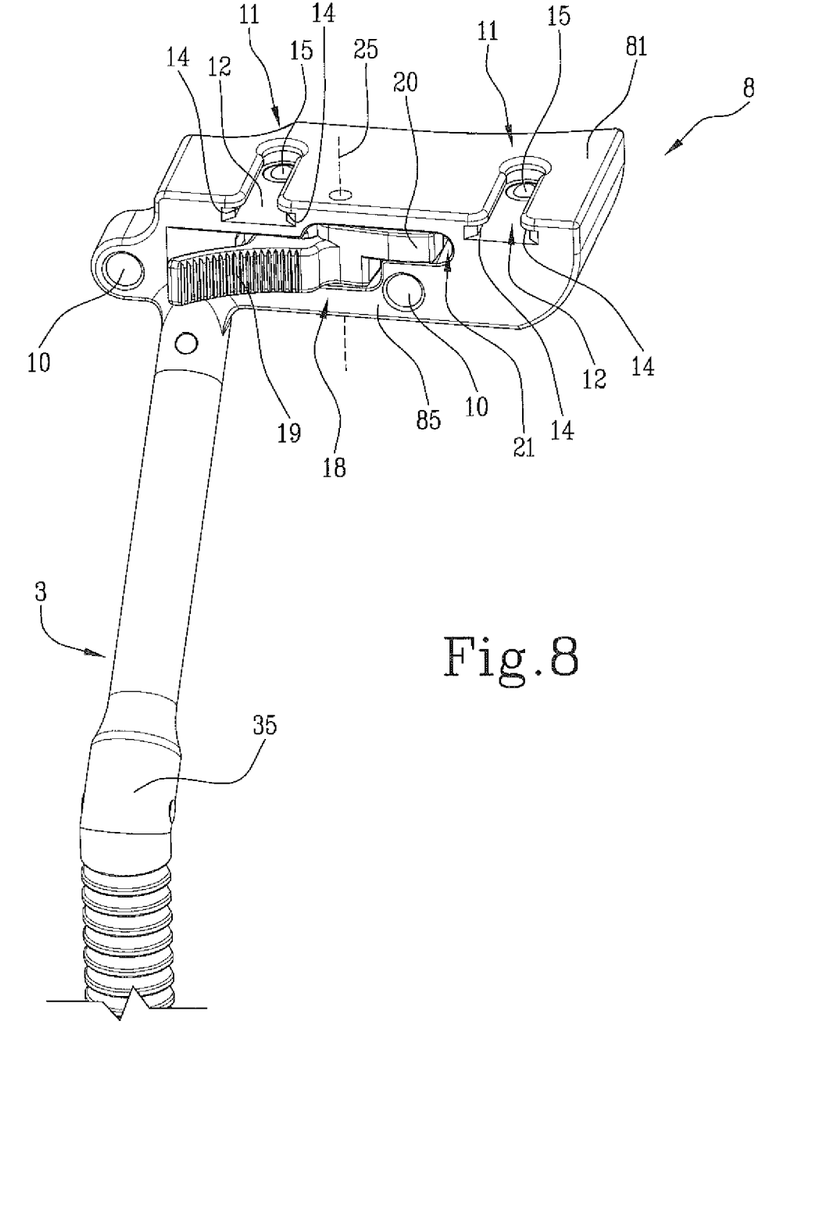
FIG. 8 is a front perspective view of the instrument according to the present invention in which the cutting guide has only one support.

Beneficially, the gauge block 9 is connected to the support 8 by means of the quick connection means 11 (FIGS. 7d and 8).

The quick connection means 11 comprise at least one rail guide 12 formed on the proximal surface 81 of the support 8 and at least one foot 13, formed on a distal surface 92 of the gauge block 9.

The foot 13, is shaped complementarily to the shape of the rail guide 12, and can be inserted into the latter in order to fasten the gauge block 9 to the support 8.

Preferably, the foot 13 has a T-shaped cross section, just as the rail guide 12 has a pair of undercuts 14 under which the head of the T of the foot 13 is inserted.

Beneficially, the rail guide 12 also has a pressing element 15 insertable into a spherical cavity 16 formed on the foot 13, to firmly lock the gauge block 9 to the support 8.

The gauge block 9 has, on its front surface 95, a tab 17 that abuts against an anterior surface 85 of support 8.

The quick connection means 11 also comprise a quick-release device 18, comprising a spring-loaded button 19 associated with the support 8 (FIGS. 5, 8, 9a and 9b).

Figures 9A, 9B:
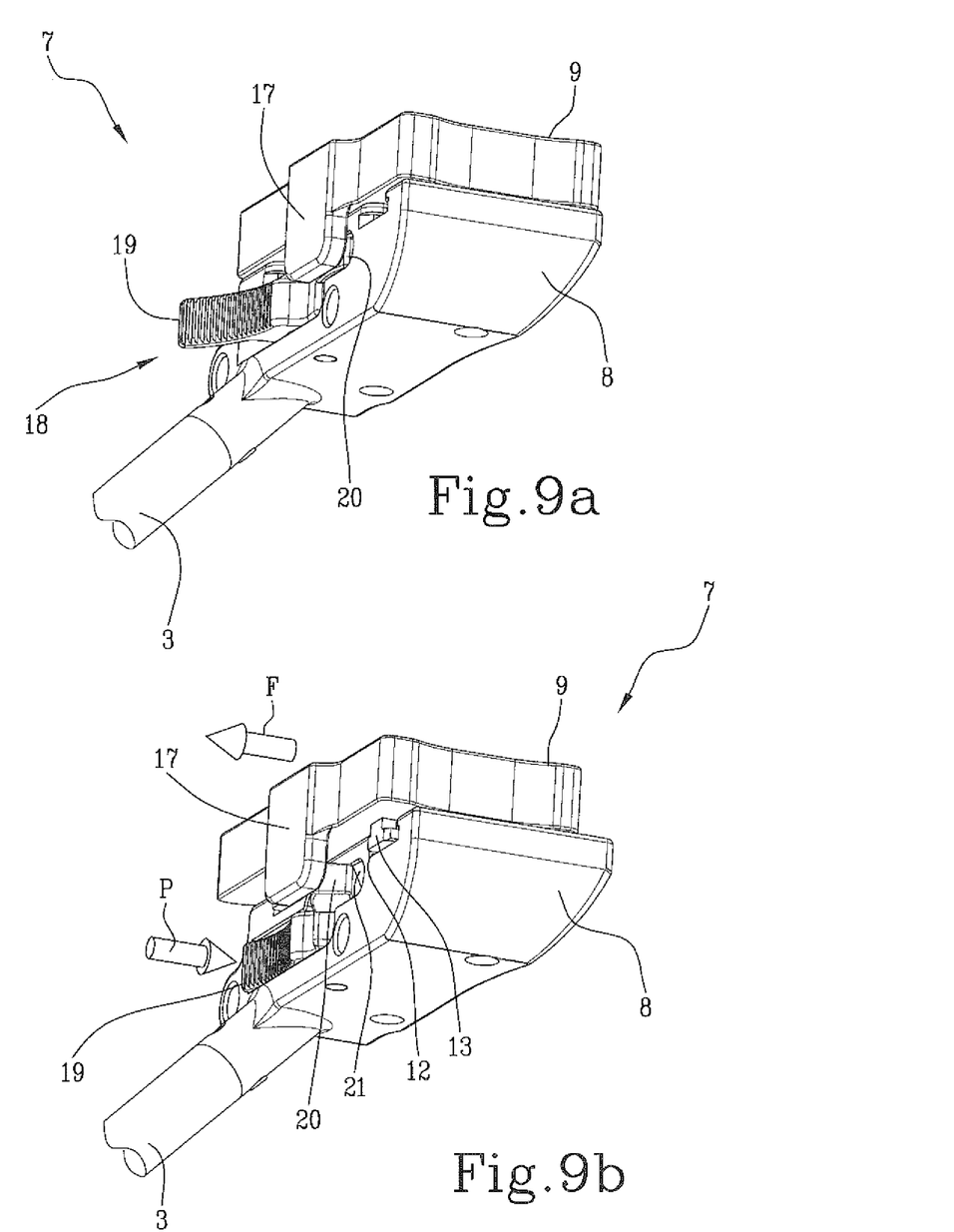
FIGS. 9a and 9b are two operating phases of removing the gauge block from the support of the cutting guide.
Figure 10:
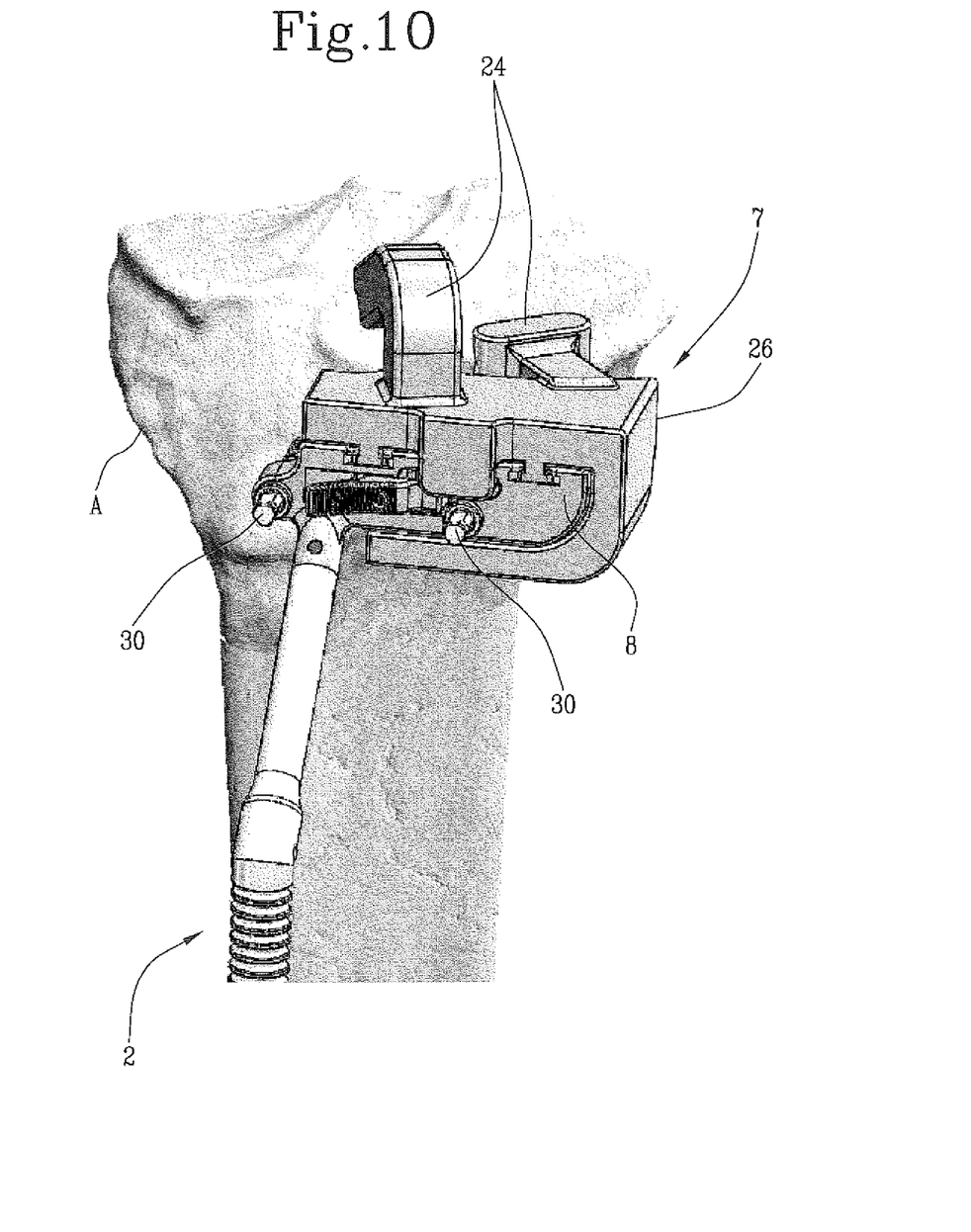

The spring-loaded button 19 is equipped with a press foot 20 that is, in the resting position, positioned inside a housing 21 formed in the support 8. As shown in FIGS. 9a and 9b, by exerting pressure on the spring-loaded button 19 (as indicated by the arrow P in FIG. 9b), the press foot 20 protrudes from the housing 21 and moves toward the tab 17, pushing it towards the outside and thus causing the release of the gauge block 9 (in the direction of the arrow F shown in FIG. 9b).

The proximal surface 91 of the gauge block 9 acts as a resting surface for the blade, which defines the cutting surface 90.

According to an alternative configuration, shown in FIG. 7e, the gauge block 9 may have a through-slot 96, inside which it is possible to insert the blade to guide it during the whole cutting operation, avoiding accidental vertical displacements and/or inclinations of the blade (FIG. 7e).

Figure 6:
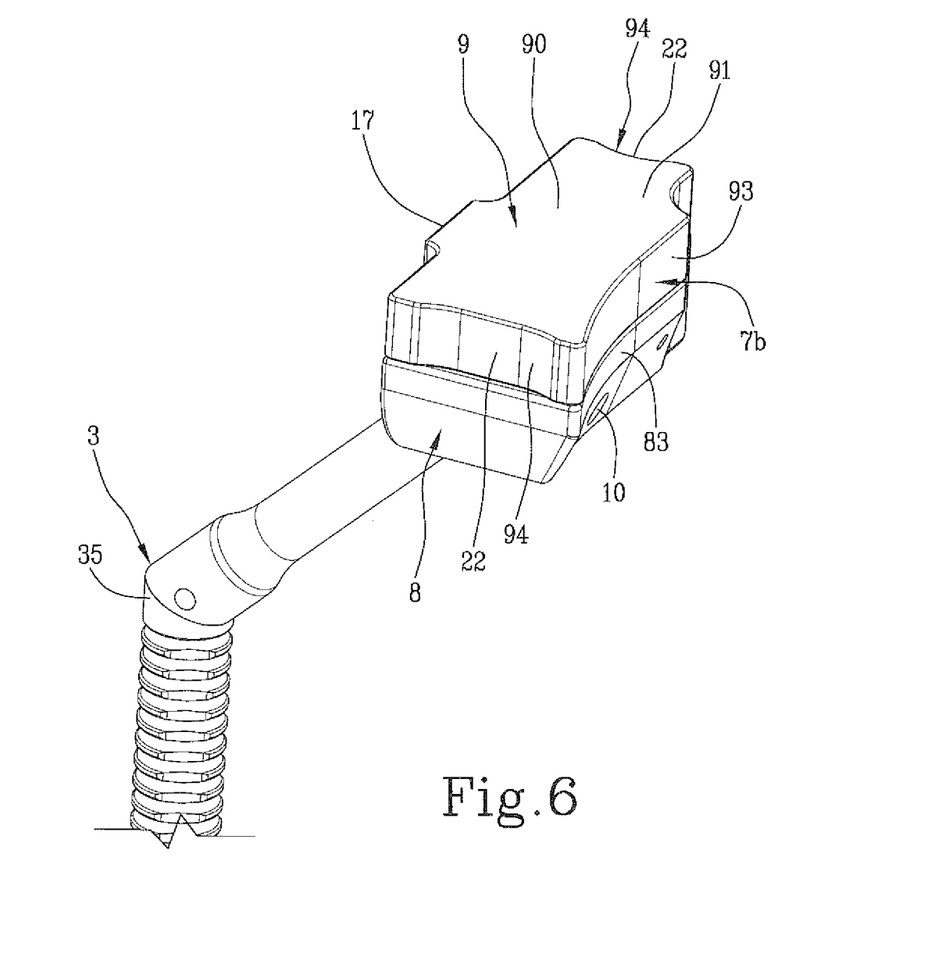
FIG. 6 is a lateral-posterior perspective view of what is shown in FIG. 5.

The cutting guide 7 has at least one posterior surface 7b, facing the patient when in use, shaped according to the anatomy of the bone to be resected, for example the tibia (as shown in FIG. 6). In other words, both the support 8 and the gauge block 9 have respective posterior surfaces 83 and 93, which together form the posterior surface 7b of the guide 7, shaped to follow, as far as possible, the anatomy of the part of the patient to be operated on.

In particular, the radii on the posterior part approximate the anatomy of the tibia, or the bone against which they will be placed, reducing the risk of contact with the patellar tendon or with other organs and making it possible to get as close as possible to the tibia or the bone to be treated. In addition, all the edges are rounded to avoid damage to the soft tissues. For a better grip, the gauge block 9 has, on its medial and lateral surfaces 94, two housings 22 which allow easy and safe grip even for blocks 9 of reduced height.

Figure 2:
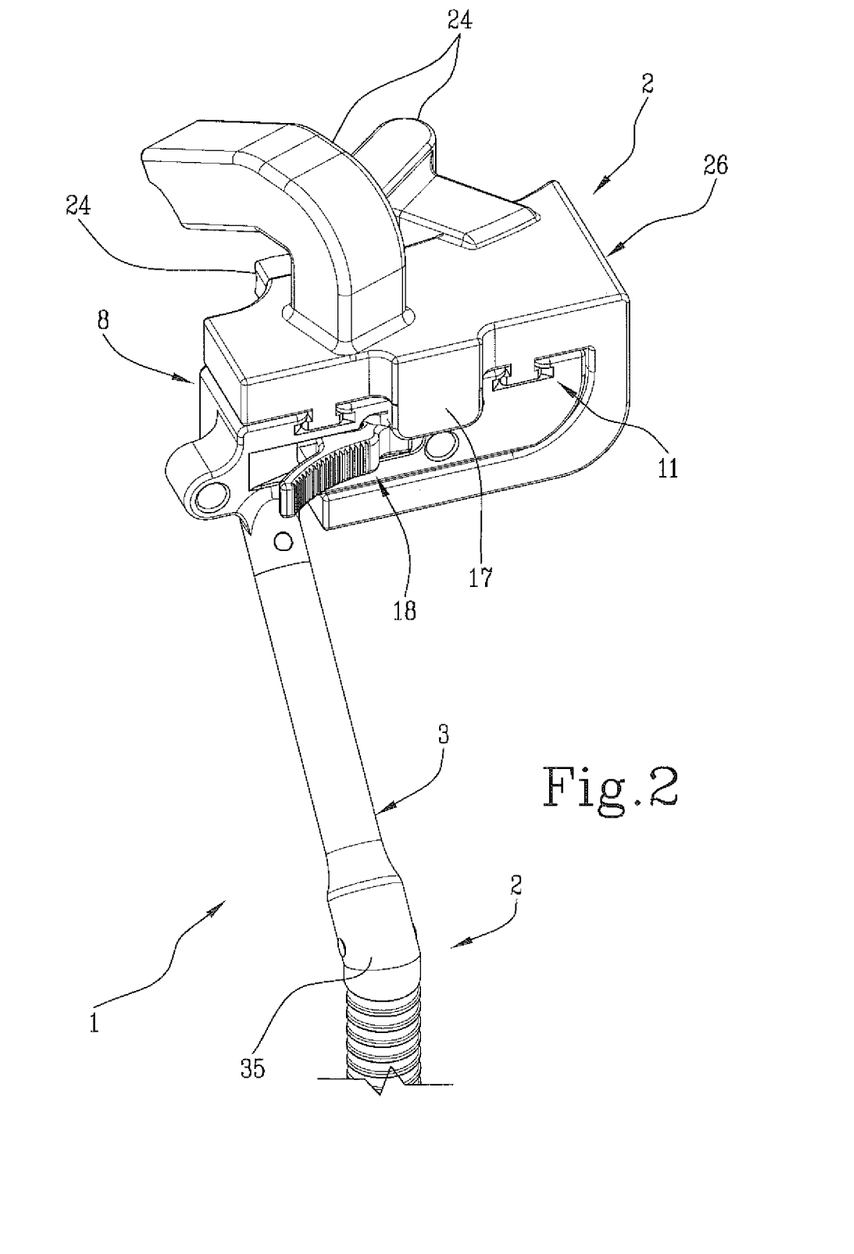
FIG. 2 is a perspective view of a detail of the instrument according to the present invention having a cutting guide associated with a patient-specific positioner.
Figure 3:
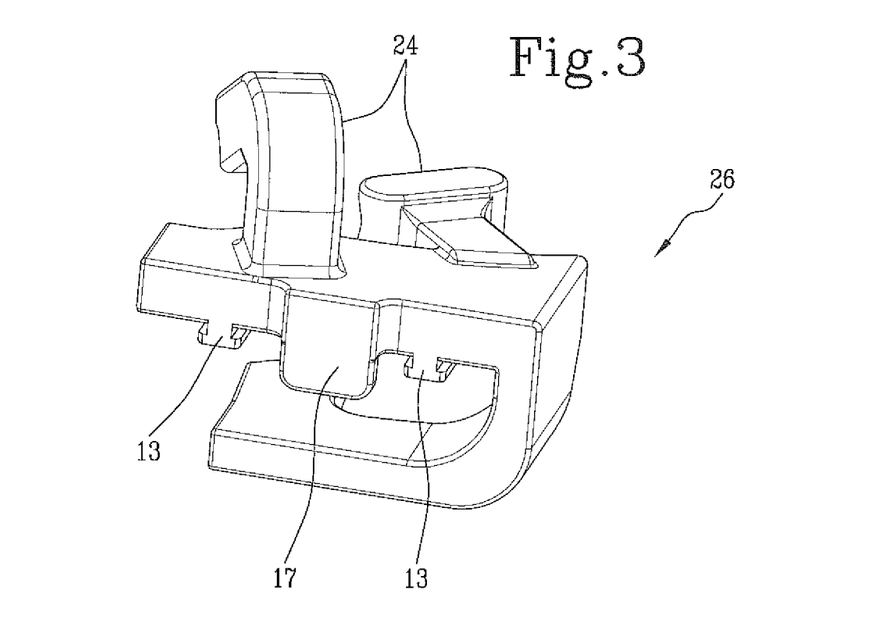
FIGS. 3 and 4 are perspective views of the patient-specific positioner illustrated in FIG. 2.
Figure 4:
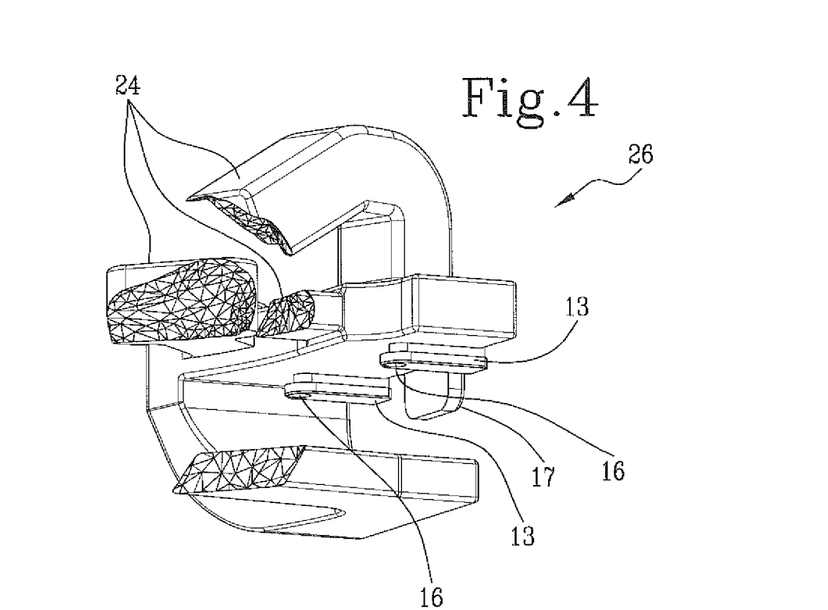
Figure 5:
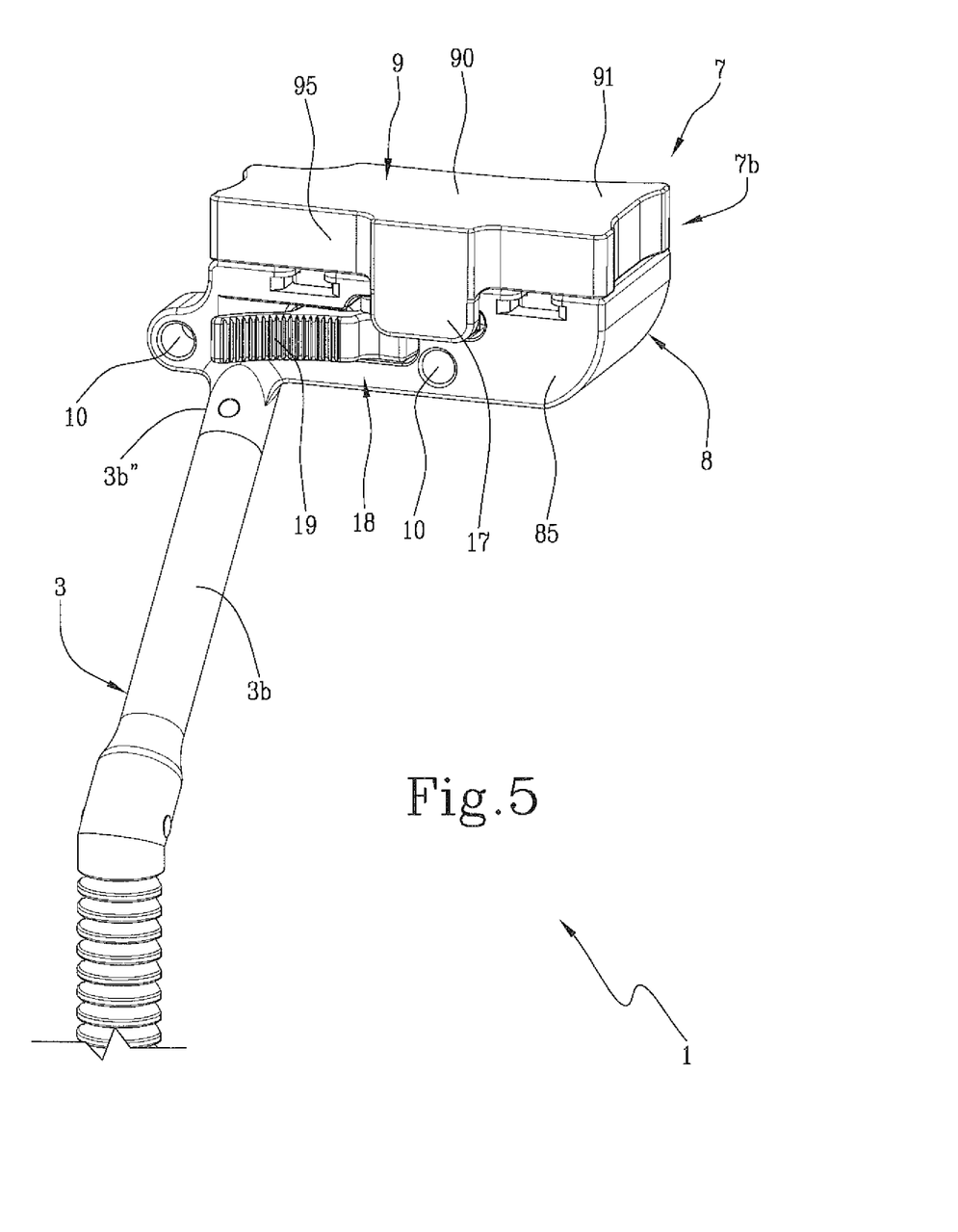
FIG. 5 is a front perspective view of part of the instrument according to the present invention having a cutting guide associated with a gauge block.

In a preferred embodiment which is illustrated in FIG. 2, the means of support and positioning 2 comprise an insert 26, also known as a patient-specific positioner, associable with the support 8 of the cutting guide 7 and having anatomical reference points 24 characteristic of the specific patient (FIGS. 3 and 4). These anatomical reference points 24, such as for example probes, abut against predetermined anatomical points of the patient in order to allow the unique and stable positioning of the instrument 1.

The gauge block 9 has a height h, measured in a direction orthogonal to the proximal surface 91, which can vary between a minimum and a maximum. The minimum and maximum height can be defined as desired depending on the operative needs. This height h is defined as the distance between the cutting plane and the distal surface 92, being the cutting plane defined, in turn, as the surface suitable for guiding the bone resection blade. According to a first embodiment, this plane, shown in FIG. 6 and indicated therein with reference 91, coincides with the proximal surface, while, in an alternative embodiment, the said cutting plane coincides with the plane defined by the cutting slot 96 as shown in FIG. 7e.

In FIGS. 7a-7c, three different gauge blocks 9 having three different heights h are shown, by way of example only.

The bone resection instrument described above is part of a bone resection kit also comprising a plurality of gauge blocks 9, alternatively associable with the support 8.

Each gauge block 9 has a thickness or height h different from the others in order to provide a series of gauge blocks 9 having heights h different from one another.

In particular, the interval by which the height of a block differs from another block is between 0.1 mm and 10 mm, preferably between 0.5 mm and 2 mm.

Consequently, the "cutting gap" that there may be between one gauge block 9 and another, and thus the gap between one cutting plane and the one that immediately follows it, used to cut further, can be between 0.1 mm and 10 mm, with the interval preferably falling in the range between 0.5 mm and 2 mm. It is however possible to have intervals of even greater than 10 mm.

Depending on which gauge block 9 is associated with the support 8, a cutting surface 90 is thus obtained, positioned at a different height depending on the thickness of the gauge block 9 used.

This makes it possible to vary the height of the cutting surface 90 without moving the support 8 and thus without removing the pins 30 or adjusting the relative position between the first portion 3a and the second portion 3b of the rod 3.

Beneficially, the cutting guide 7, and in particular the support 8, is removably attached to the second portion 3b.

The latter has an elbow 35 that projects the cutting guide 7 into close proximity with the patient.

After assembling the means of support and positioning 2, connecting together the first portion 3a and the second portion 3b of the rod 3, a gauge block 9 of predetermined height is associated with the support 8, positioned at the top of the rod 3.

The gauge block 9 is connectable to the support by means of the quick connection means 11. In detail, the feet 13 of the block 9 are inserted by T-connection inside the respective rail guides 12 present on the support 8 (FIGS. 7d, 8).

The block 9 is pushed and made to slide on the support 8, gliding along the rails until the end of their run, i.e. until each foot 13 arrives at the end of the rail guide 12.

In this position, the pressing element 15 of the rail guide 12 is inserted into the respective spherical cavity 16 formed on the foot 13, stably securing the gauge block 9 to the support 8.

Still in this position, the tab 17 of the block 9 abuts the anterior surface 85 of the support 8, thus being positioned in front of the press foot 20 and closing off access to the housing 21.

To easily remove and extract the block 9 from the rails 12 in order to replace it with another one of a different height, the quick-release device 18, is activated, in particular, the spring-loaded button 19 (FIG. 9b) is pressed.

The spring-loaded button 19 is hinged along an axis 25 and continues beyond the latter with the press foot 20 making up one part of it.

In the resting position the press foot 20 is contained inside the support 8, while the spring-loaded button 19 protrudes from the anterior surface 85 of the support 8. Acting on the spring-loaded button 19, pushing it towards the anterior surface 85 of the support 8, causes the simultaneous rotation of the press foot 20 around the pivot axis, causing it to protrude from its housing 21.

The press foot 20 thus acts on the tab 17, moving the gauge block 9 which disengages from the support 8.

By gripping the gauge block 9 by its lateral housings 22 it is possible to slip it completely off its support and replace it with another one having a different height.

It is not necessary to remove the guide 7 from the bone or to remove the pins 30 to perform these operations.

The bone resection instrument can be used in two different fields of application: the first is with a conventional (nonpatient-specific) positioning system, the second is with a patient-specific positioning system.

In both cases, the cutting guide 7 consists of the support 8 attached to the bone and the insert or gauge block 9 (or shim) assembled with the support 8 by means of the quick connection means 11.

The upper plane or the proximal surface 91 of the gauge block 9 or the plane defined by the cutting slot 96 formed in it, define, as abovementioned, the level of the bone resection. The level of the bone resection with respect to the support 8 is determined by the thickness h of the block 9: gauge blocks 9 of different thickness determine different resection levels.

The difference between the conventional positioning system and the patient-specific positioning system is that in the first case the cutting guide 7 can be connected to intramedullary or extramedullary means of support and positioning 2 that allow its position to be defined in accordance with the cutting parameters (slope angle, varus/valgus angle and initial desired cut height) and defined in the operating room with respect to anatomical references (e.g. ankle, anatomical axis of the tibia, inclination of tibial trays, etc.).

The surgical technique requires that once the cutting parameters (angle of slope, varus/valgus and minimum cut height) have been defined, the support 8 is positioned accordingly and attached to the bone by means of pegs or pins that are inserted inside the positioning holes 10 in the support 8.

The cut height parameter can be changed by using a gauge block having a different thickness or height h, without the need to remove and reposition the support 8 which remains attached to the bone.

Thanks to this instrument, the magnitude of the change in cut height is no longer constrained by geometrical limits (that in the majority of cases involve a minimum change in cutting level of 2 mm) but is instead determined by changing the thickness of the individual gauge blocks 9.

It also avoids continuous repositioning of the guide and the consequent risks of misaligning the resection instrument.

In the second case, the cutting guide 7 can be connected to a patient-specific positioning system.

In this case, the cutting guide 7 comprises the aforementioned patient-specific positioner 26, which is an insert having anatomical reference points 24 typical of the patient (e.g. osteophytes) which are used as reference points for its unique and stable positioning (FIGS. 2-4 and 10).

The patient-specific positioner 26 is constructed on the basis of a pre-operative analysis of the solid geometry of the patient's bone.

This makes it possible to position the cutting guide 7 in such a way that the resection is aligned and complies with the cutting parameters defined pre-operatively (slope angle, varus/valgus, minimum cut height).

Once the precise position is found, the guide 7 can be attached to the bone by means of pegs 30 inserted into the holes 10 present in the support 8.

The resulting position of the guide will be established and will match the one defined in the pre-operative phase by means of reconstruction.

After attaching the support 8 to the bone, the positioner 26 can subsequently be removed while maintaining the cutting guide 7 in position. The positioner 26 is associated with the support 8 in exactly the same way as the gauge block 9 is associated with the support 8, i.e. by the quick connection means 11.

The feet 13 of the positioner 26 are inserted by T-connection into the corresponding rails 12 of the support 8. The positioner 26 is slid along the rails 12 until the two pressing elements 15 present on the support 8 are inserted into the two spherical cavities 16 at the end of the feet of the positioner 26.

The positioner 26 also has a tab 17 on its anterior part which is pushed into abutment against the anterior surface 85 of support 8.

The release mechanism of the patient-specific positioner 26 is thus also similar to that of the release mechanism of the gauge block 9: it uses the quick-release device 18 previously described.

With the patient-specific positioner 26 removed, it is possible to associate a gauge block 9, that defines the cutting surface 90, with the support 8.

At this point, the first cut can be carried out.

The cut height can then be varied by quickly interchanging blocks 9 of different thicknesses (FIGS. 7a-7c).

In use, after arranging the means of support and positioning 2, the cutting guide 7 is assembled, connecting a gauge block 9 of greater height to the support 8 (e.g. thickness marked +0 mm).

Subsequently, the cutting parameters (slope angle, varus/valgus, minimum cut height) are defined using the "eyeballing" technique or the extramedullary/intramedullary reference system.

When the position of the guide 7 is satisfactory, the cutting guide is secured to the bone by means of two pegs.

The cutting parameters are thus established. The alignment rod 3 is preferably used to check the slope angle and varus/valgus. The cut height can be varied by interchanging a gauge block 9 for one of a different thickness. At this point, the cutting parameters being verified, the bone resection can be carried out, supporting the blade directly on the proximal surface 91 of the block 9 or by inserting the blade in the cutting slot 96, if present.

Beneficially, to avoid excessive resections, it is preferable to begin with a gauge block 9 having a greater thickness and proceeding to progressively replace the gauge blocks 9 with ones having smaller heights. The position of the cut can thus be varied in a gradual and controlled way.

Figure 11:
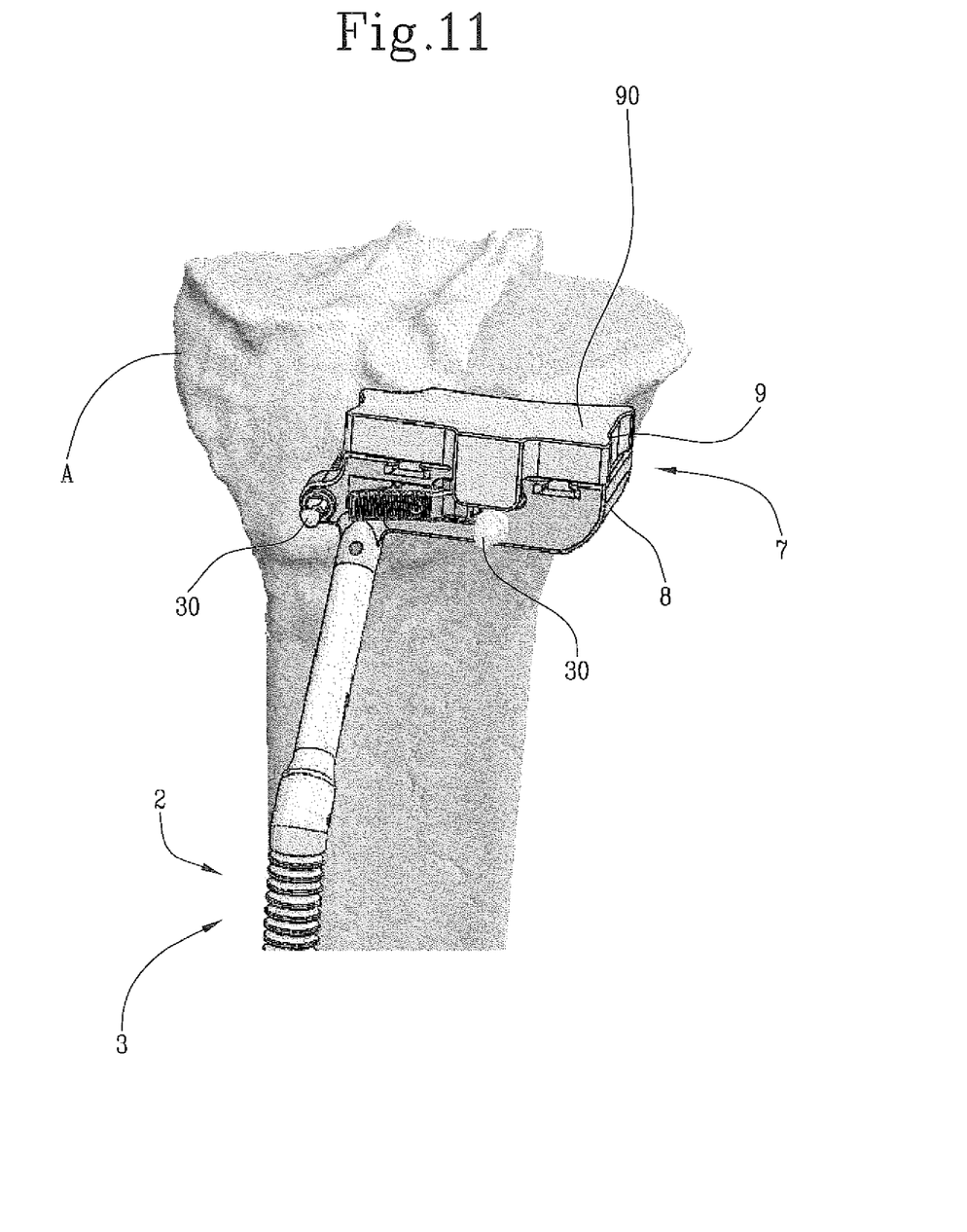
FIGS. 11 and 12 are two representations of the instrument of the present invention according to the configuration illustrated in FIG. 5 in use, in which the cutting guide is associated with two different gauge blocks, one having a greater thickness than the other to define different heights for the cutting surface.
Figure 12:
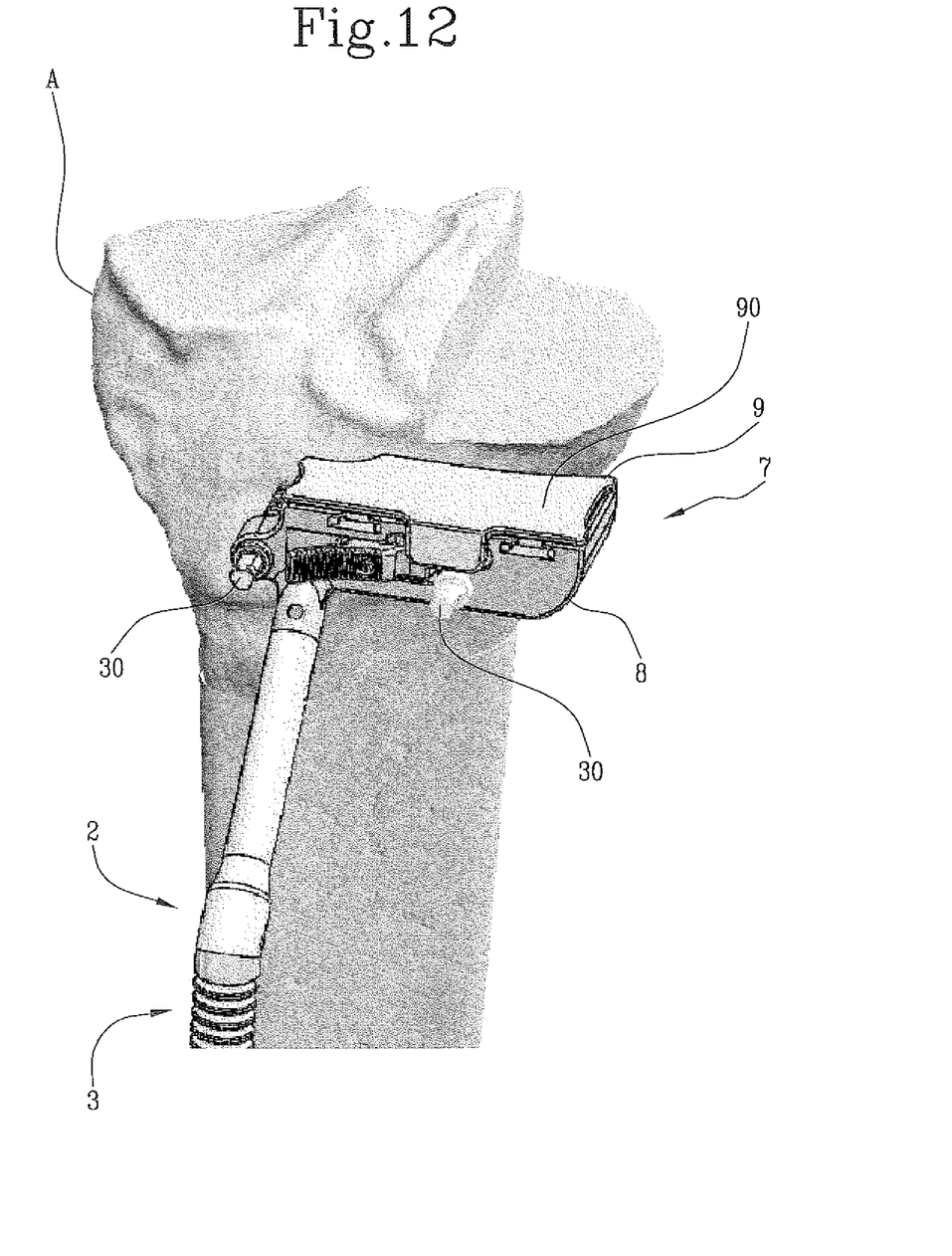

Therefore, after having positioned the first block 9 and having carried out the first resection, a check is made to see if it has taken place satisfactorily (e.g. the quality of the bone occurring at the level of the cut and the tightness occurring in flexion-extension are satisfactory, sufficient thickness has been removed to permit implantation of the prosthesis). If the resection performed appears unsatisfactory, the cut height is decreased by replacing the block 9 in use with one of a lower height, without repositioning the support 8 attached to the bone (FIGS. 11 and 12).

A further resection is then performed. If it is still unsatisfactory, blocks of successively smaller height are iteratively used until the optimal cut height is achieved.

Figure 13:
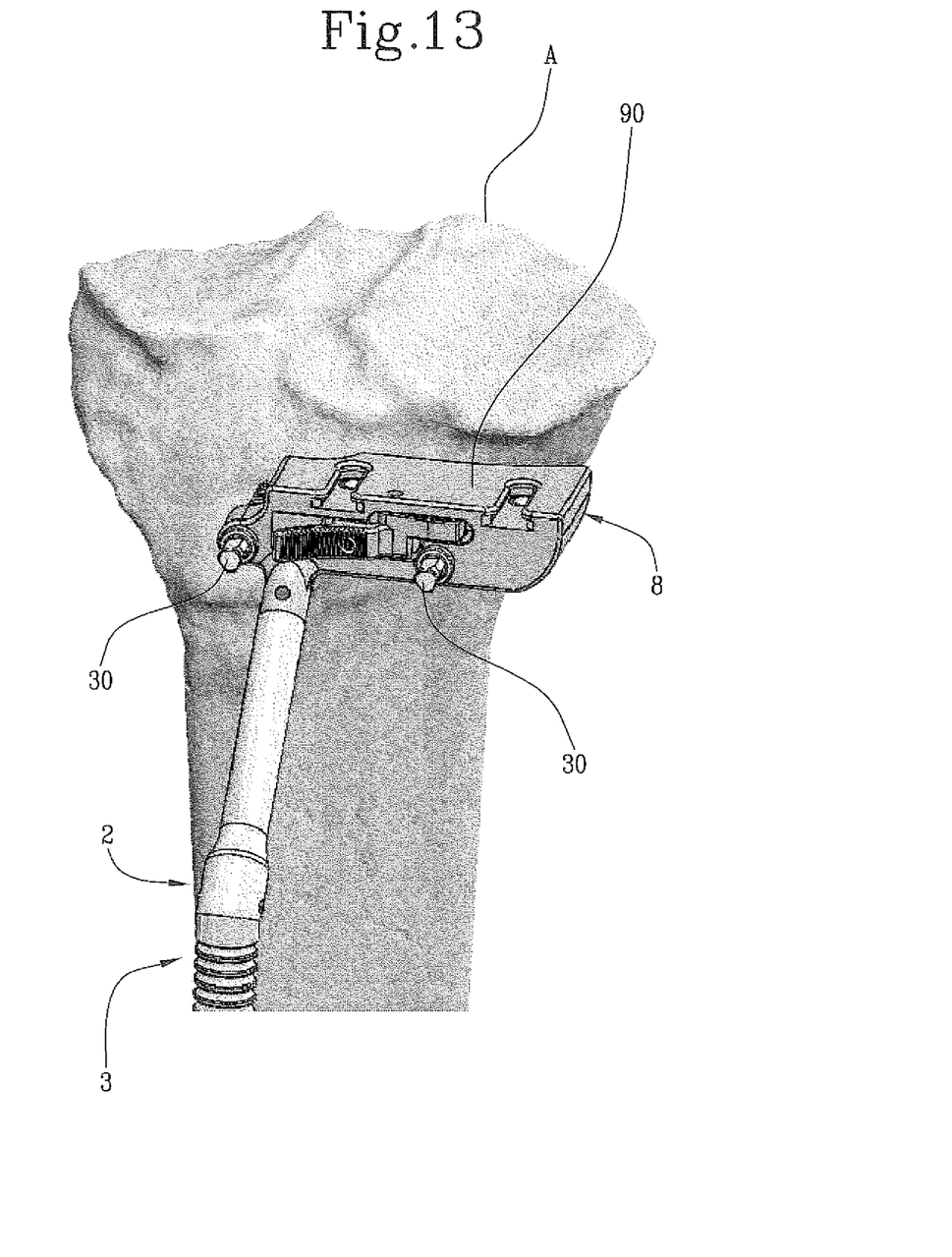
FIG. 13 represents the instrument of the present invention according to the configuration illustrated in FIG. 8, in which the cutting guide has only one support: this may be the situation which precedes the coupling of the support with a gauge block, possibly after the removal of the patient-specific positioner, or is the limiting configuration of the instrument which is the subject of the present invention in use: in order to have the cutting surface as low as possible, the gauge block is removed and the proximal surface of the support is used as a cutting surface.

The minimum cut height can be obtained without changing the position of the support 8 and by using the proximal surface 81 of the same support 8 as the cutting plane (FIG. 13).

The surgical technique with the use of the patient-specific positioner 26 is similar to the one just described.

The differences are that, following a CT/MRI scan of the joint, pre-operative planning of the operation is carried out: definition of the size, slope, varus/valgus, minimum cut height. In the operating room, the positioner 26 is mated with the support 8 of the cutting guide 7. Then the positioner 26 is manually positioned. The positioner is unique: the correct position is the one that ensures greatest stability between the positioner 26 and the bone, thus resulting in an optimum and stable positioning of the guide 7. Once the position is satisfactory, the cutting guide 7 is attached to the bone by means of two pegs attached through the holes 10 of the support 8.

At this point, it is possible to remove the positioner 26 and connect the gauge block 9 to the support 8. From this point onwards it continues as just described, using a first gauge block 9 of greater height and performing a first cut.

The level of bone resection is assessed and is continued by replacing the block 9 in use with ones having progressively smaller heights h until the suitable cut height is reached (FIGS. 11 and 12).

The height h of the gauge block 9 determines the level of the cutting plane, which can be varied by using a different height block 9 each time. With this system of just interchanging blocks 9 of different thicknesses, it is possible to vary the level of resection in discrete steps from 0.1 mm to 10 mm, with a guarantee of constancy of alignment and without having to remove and replace the support 8 each time.

The thickness variation between the different blocks present in the instrumentation available to the surgeon and thus the variation of the cutting level, obtainable by interchanging blocks 9 of different thicknesses, can be defined as desired (preferably between 0.5 mm and 2 mm).

The cutting guide 7 can be made in right-medial/left-lateral or left-medial/right-lateral configuration, to be used according to the joint being operated on. The reduced dimensions and contoured design make it suitable for use in various surgical approaches, also including minimally invasive procedures and in unicompartmental arthroplasty.

The invention makes it possible to secure many benefits and attain its intended purposes.

The bone resection instrument of the present invention makes it possible to change the level of resection, avoiding continuous and repeated repositioning of the support and therefore of the cutting guide during the entire duration of the operation.

The invention makes it possible to vary the level of the tibial bone resection, once the cutting guide is positioned, so as to avoid repeated repositioning of the guide and the consequent risks of changing the defined cutting parameters and/or misalignment of the resection instrument.

With this technique, less invasive, shorter surgical procedures can be achieved for the patient, with the possibility of defining micrometric cutting variations, avoiding the need to provide for repositioning of the fixation pin of the guide.

With the bone resection instrument according to the present invention, once the guide is positioned and attached, it is possible to change the magnitude of the cut height so as to make it possible to perform a minimal and conservative cut.

The magnitude of the variation of the cut height is no longer constrained by the inherent geometrical limits in the guide or in the conventional repositioning and/or fastening systems, (which, in the instruments currently commercially available, impose a repositioning of the guide with minimum variation of 2 mm), but is instead determined by the different thicknesses of the gauge blocks; the difference between the different thicknesses can be between 0.1 mm and 10 mm, preferably between 0 mm and 2 mm.

The invention claimed is:

1. An instrument for bone resection, comprising:
   a supporting and positioning system for maintaining the correct alignment of said instrument with respect to a bone to be cut, said supporting and positioning system comprising a base and a rod coupled to the base; and
   a cutting guide, connected to said rod, the cutting guide comprising:
      a support attachable to the bone to be cut, and
      a gauge block having a cutting surface and removably connected to said support,
      wherein said gauge block is connected to said support by a quick connection system that comprises a quick-release device comprising a spring-loaded button equipped with a press foot that acts on a tab, wherein said tab projects from an anterior surface of the gauge block and abuts against an anterior surface of said support to cause the immediate release of said gauge block.

2. The instrument according to claim 1, wherein said quick connection system further comprises at least one guide rail formed on a proximal surface of said support and at least one foot, formed on a distal surface of said gauge block, insertable into said guide rail and shaped to match a shape of said guide rail.

3. The instrument according to claim 2, wherein said guide rail has a pressing element insertable into a spherical cavity realized on said foot, to firmly lock the gauge block to said support.

4. The instrument according to claim 1, wherein said gauge block has a cutting through-slot, inside which a blade may be inserted.

5. The instrument according to claim 1, wherein said gauge block has a proximal surface defining the cutting surface.

6. The instrument according to claim 1, wherein said supporting and positioning system governs a spatial position of said cutting guide.

7. The instrument according to claim 1, wherein said cutting guide has at least one posterior surface, facing towards a specific patient when in use, shaped according to the anatomy of the specific patient.

8. The instrument according to claim 1, wherein said supporting and positioning system comprises a patient-specific positioner, which may be associated with the support of the cutting guide, providing anatomical reference points characteristic of a patient, in order to allow unique and stable positioning of the instrument.

9. The instrument according to claim 1, said gauge block comprises two lateral seats to allow an easier grip of the same.

* * * * *